United States Patent [19]

Hillard et al.

[11] 4,064,102
[45] Dec. 20, 1977

[54] LIGHT AND HEAT STABILIZERS FOR POLYOLEFINS

[75] Inventors: Ray Leonard Hillard, Annandale; William Baptist Hardy, Bound Brook, both of N.J.

[73] Assignee: American Cyanamid Company, Stamford, Conn.

[21] Appl. No.: 668,156

[22] Filed: Mar. 18, 1976

[51] Int. Cl.² .................. C07D 211/62; C07D 401/02; C08K 5/34
[52] U.S. Cl. .......................... 260/45.8 N; 260/293.63; 260/293.64; 260/293.88
[58] Field of Search ...................... 260/45.8 N, 293.88, 260/293.63

[56] References Cited

U.S. PATENT DOCUMENTS

| | | | |
|---|---|---|---|
| 591,483 | 10/1897 | Merling | 260/293.88 |
| 2,759,942 | 8/1956 | Krapcho | 260/293.88 |
| 3,534,048 | 10/1970 | Murayama et al. | 260/293.63 |
| 3,684,803 | 8/1972 | Kuhnis et al. | 260/293.88 |
| 3,850,877 | 11/1974 | Cook | 260/45.8 N |
| 3,887,517 | 6/1975 | Murayama et al. | 260/45.8 N |
| 3,929,804 | 12/1975 | Cook | 260/45.8 N |
| 3,959,291 | 5/1976 | Cook | 260/45.8 N |

OTHER PUBLICATIONS

Noller, Chemistry of Organic Compounds, 2nd Edition, 1957, p. 254.
Sperber et al., J.A.C.S., vol. 81, 1959, pp. 704–709.

*Primary Examiner*—Donald E. Czaja
*Assistant Examiner*—R. A. White
*Attorney, Agent, or Firm*—Frank M. Van Riet; Philip Mintz

[57] ABSTRACT

Compounds of the formula:

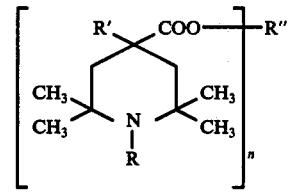

wherein R is hydrogen or alkyl ($C_1$–$C_8$), R' is hydrogen, hydroxyl or lower alkoxy ($C_1$–$C_8$); R" is alkyl ($C_1$–$C_{20}$), alkylene ($C_2$–$C_{12}$), cycloalkyl, wherein the alicyclic ring contains 5- or 6-carbon atoms, cycloalkylene, wherein the alicyclic ring may contain lower alkyl substituents, alkenyl ($C_3$–$C_{20}$), arylene or aralkylene; n is an integer from 1 to 4, are useful for stabilizing polyolefin polymer against photo and thermal degradation.

9 Claims, No Drawings

LIGHT AND HEAT STABILIZERS FOR POLYOLEFINS

This invention relates to esters of 2,2,6,6-tetramethyl-piperidine-4-carboxylic acid, and more particularly to esters represented by formula (I):

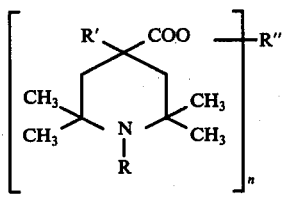

where R is hydrogen or alkyl ($C_1$–$C_8$); R' is hydrogen, hydroxyl or alkoxy ($C_1$–$C_8$); R'' is alkyl ($C_1$–$C_{20}$), alkylene ($C_2$–$C_{12}$), cycloalkyl, wherein the cycloaliphatic ring contains 5- or 6-carbon atoms, cycloalkylene, wherein the cycloaliphatic ring may contain lower alkyl substituents, arylene, aralkylene and alkenyl ($C_3$–$C_{20}$); n is an integer from 1 to 4.

The invention also relates to the use of these esters as stabilizers against photo- and thermal degradation, particularly against degradation induced by UV light, of synthetic polymers, especially polyolefins. The invention further relates to polymer compositions stabilized by the incorporation therein of said esters.

Stabilizers for synthetic and naturally occurring polymers, including UV stabilizers, have been the subject of continuing investigation for many years, and numerous compounds have been suggested for such purpose. Recent patent literature has described a considerable number of stabilizer compounds which are derivatives of hindered amines of the type:

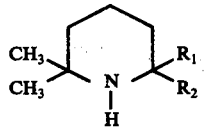

wherein $R_1$ and $R_2$ may be the same or different and represent an alkyl of 1 to 4 carbon atoms. Of particular interest is 2,2,6,6-tetramethylpiperidine and its derivatives.

U.S. Pat. No. 3,640,928 (Murayama to Sankyo Company, Ltd.) particularly describe esters, and their use in stabilizing polymers, of the type represented by formula (II):

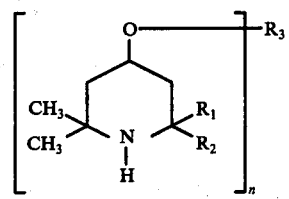

wherein $R_1$ and $R_2$ are as defined above; $R_3$ is an acyl, diacyl or triacyl group derived from aliphatic, alicyclic or heterocyclic mono-, di- or tricarboxylic acids; n is 1 to 3.

We have now discovered, quite unexpectedly, that esters of formula (I) provide superior stabilizing properties against photodegradation of synthetic polymers, particularly polyproplylene, as compared with the esters of formula (II).

It is surprising and unexpected that esters of 2,2,6,6-tetramethylpiperidine-4-carboxylic acid, as represented by (I), are superior to esters of 2,2,6,6-tetramethyl-4-hydroxypiperidine, as represented by (II).

In the above formula (I), when n is 1, R'' is a monovalent aliphatic or cycloaliphatic radical derived from an aliphatic or cycloaliphatic alcohol. Representative alcohols include methanol, ethanol, n-propanol, isopropanol, n-butanol, sec. butanol, tert. butanol, amyl alcohol, isoamyl alcohol, neopentyl alcohol, n-hexanol, n-octanol, 2-ethylhexyl alcohol, n-decyl alcohol, n-dodecyl alcohol, stearyl alcohol, eicosanol, and the like; cyclopentanol, cyclohexanol, methyl cyclohexanol, and the like.

When n is 2, R'' is a divalent alkylene, cycloalkylene, arylene or aralkylene radical derived from an alkanediol, cycloalkanediol, dihydric phenol or aralkylene diol. Representative of such diols are ethylene glycol, 1,2- and 1,3- propane diol, 1,4-butanediol, neopentyl glycol, 1,6-hexanediol, 1,8-octanediol, 1,10-decanediol, cyclopentanediol, 1,4-cyclohexanediol, 1,4-cyclohexane dimethanol, 1,4-cyclohexanediethanol, and the like; hydroquinone, α,α-xylylene glycol, and the like. Also included within the definition of R'' are radicals derived from diols containing a heteroatom in the chain, such as thiodiethanol, diethanolamine, and diethylene glycol.

When n is 3 or 4, R'' is a trivalent or tetravalent aliphatic radical derived from an aliphatic polyol. Representative of such polyols are glycerol, trimethylolpropane, pentaerythritol, and the like.

The term "synthetic polymer", as used herein is intended to include polyolefins, and particularly poly-α-olefins, such as polyethylene, polypropylene, polybutylene and copolymers thereof, for example, ethylenepropylene copolymer. Also intended are polyolefins such as polystyrene, polybutadiene, polyisoprene, and the like, and copolymers, such as ethylene-vinylacetate copolymers, styrene-butadiene copolymers, acrylonitrile-butadienestyrene polymers (ABS plastics), and the like. The invention is particularly directed to the stabilization of polypropylene.

The compounds of formula (I) may be prepared readily by conventional esterification of the carboxylic acid (III):

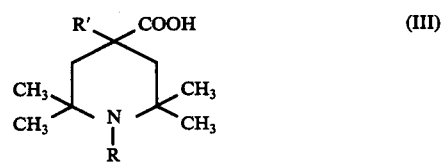

The carboxylic acid (III) may be obtained in accordance with procedures similar to those described by Sadyky-Zade et al, Zh, Organ. Khim. 9, 1841–44 (1973), U.S. Pat. No. 3,274,227, or Weizmann et al, J. Am. Chem. Soc. 70, 1153–58 (1948), whereby 2,2,6,6-tetramethylpiperidin-4-one (IV) is reacted with chloroform in the presence of a base to form the corresponding 4-trichloromethyl-4-hydroxy derivative (V) followed by hydrolysis of (V) in the presence of water or an alcohol, such as methanol, to give the carboxylic acid (III), where R' is hydroxyl or alkoxy.

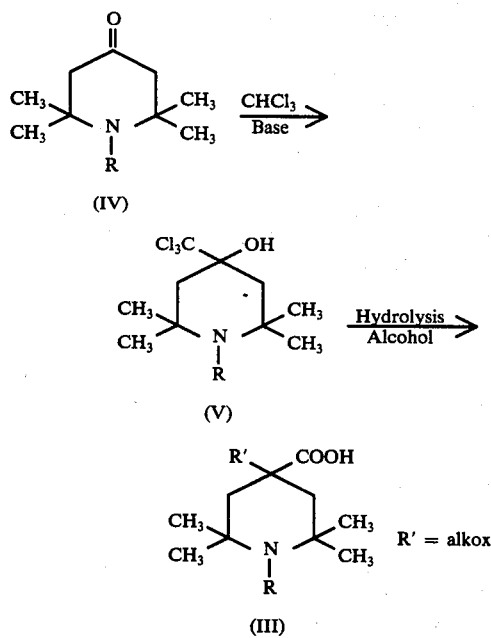

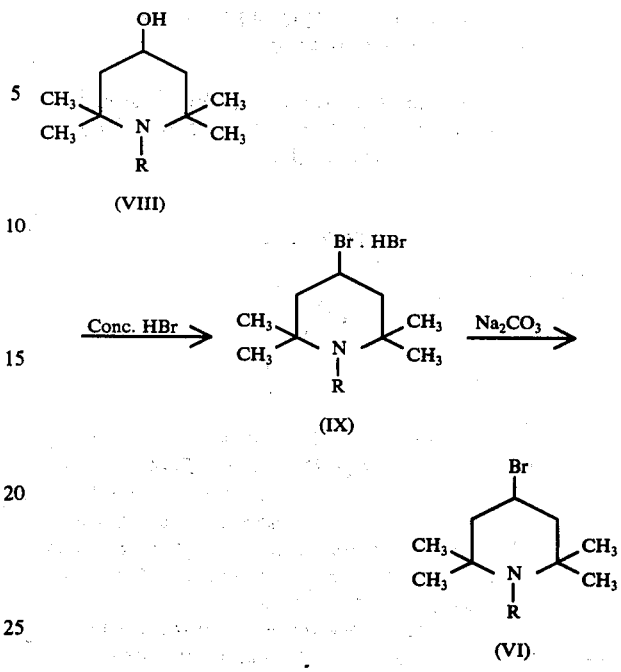

The intermediate carboxylic acid (III), wherein R' is hydrogen, may be prepared in accordance with procedures similar to those described by Simchen et al in Synthesis, 1975, No. 9, pages 605-607, whereby the 4-bromo compound (VI) is reacted with a tetraalkylammonium cyanide, such as tetraethylammonium cyanide, in a suitable solvent, such as dichloromethane, acetonitrile or dimethyl sulfoxide, followed by hydrolysis of the nitrile (VII).

Compound (III) wherein R' is hydroxyl may also be prepared in accordance with procedures similar to those described by Nazarov et al, J. Gen. Chem. U.S.S.R. (English), 26, 3877–3889 (1956) whereby the ketone (IV) is reacted with potassium cyanide in the presence of an acid to produce the corresponding cyanohydrin (X) which may then be hydrolyzed to the hydroxy acid.

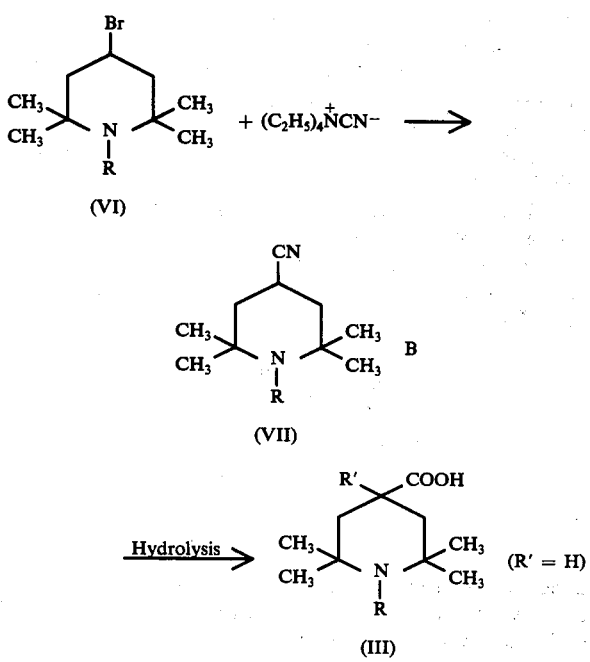

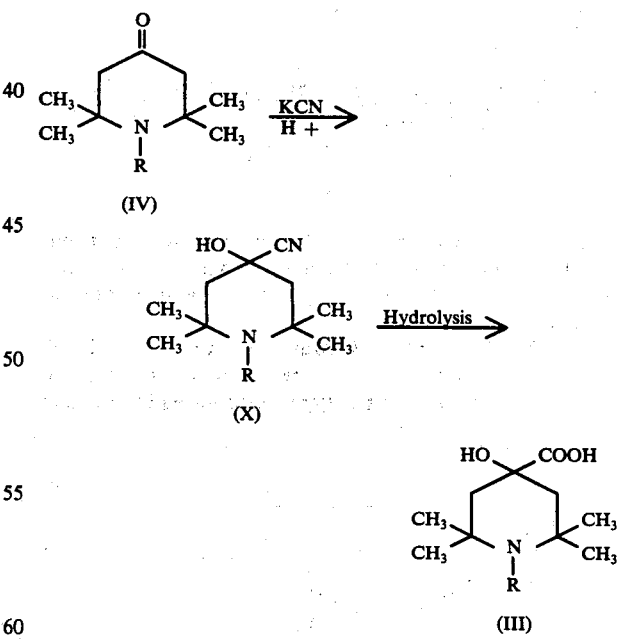

The 4-bromo compound (VI) is readily obtained by reaction of 2,2,6,6-tetramethylpiperidin-4-ol (VIII) with conc. hydrobromic acid to form the 4-bromo hydrobromide salt (IX), which is then neutralized with a base, e.g. sodium carbonate.

Representative examples of the ester derivatives of this invention are listed below. It is, however, to be understood that the invention is not limited thereto.
1. methyl 2,2,6,6-tetramethylpiperidine-4-carboxylate
2. n-butyl 2,2,6,6-tetramethylpiperidine-4-carboxylate
3. n-octyl 2,2,6,6-tetramethylpiperidine-4-carboxylate
4. stearyl 2,2,6,6-tetramethylpiperidine-4-carboxylate 5. cyclopentyl 2,2,6,6-tetramethylpiperidine-4-carboxylate
6. cyclohexyl 2,2,6,6-tetramethylpiperidine-4-carboxylate
7. 4-methylcyclohexyl 2,2,6,6-tetramethylpiperidine-4-carboxylate
8. allyl 2,2,6,6-tetramethylpiperidine-4-carboxylate
9. ethyl 2,2,6,6-tetramethylpiperidine-4-hydroxy-4-carboxylate
10. n-hexyl 2,2,6,6-tetramethylpiperidine-4-hydroxy-4-carboxylate
11. cyclohexyl 2,2,6,6-tetramethylpiperidine-4-hydroxy-4-carboxylate
12. allyl 2,2,6,6-tetramethylpiperidine-4-hydroxy-4-carboxylate
13. isopropyl 2,2,6,6-tetramethylpiperidine-4-methoxy-4-carboxylate
14. 2-ethylhexyl 2,2,6,6-tetramethylpiperidine-4-ethoxy-4-carboxylate
15. stearyl 2,2,6,6-tetramethylpiperidine-4-butoxy-4-carboxylate
16. cyclohexyl 2,2,6,6-tetramethylpiperidine-4-octyloxy-4-carboxylate
17. 1,2-ethylene 2,2,6,6-tetramethylpiperidine-4-carboxylate
18. 1,4-butylene 2,2,6,6-tetramethylpiperidine-4-carboxylate
19. 1,6-hexamethylene 2,2,6,6-tetramethylpiperidine-4-carboxylate
20. 2-butylene 2,2,6,6-tetramethylpiperidine-4-carboxylate
21. thiodiethylene 2,2,6,6-tetramethylpiperidine-4-carboxylate
22. 1,4-cyclohexylene 2,2,6,6-tetramethylpiperidine-4-hydroxy-4-carboxylate
23. 2-butylene 2,2,6,6-tetramethylpiperidine-4-hydroxy-4-carboxylate
24. iminodiethylene 2,2,6,6-tetramethylpiperidine-4-ethoxy-4-carboxylate
25. oxydiethylene 2,2,6,6-tetramethylpiperidine-4-octyloxy-4-carboxylate
26. 2-ethyl-1,2,3-propanetriyl 2,2,6,6-tetramethylpiperidine-4-carboxylate
27. neopentanetetrayl 2,2,6,6-tetramethylpiperidine-4-hydroxy-4-carboxylate
28. 2-ethyl-1,2,3-propanetriyl 2,2,6,6-tetramethylpiperidine-4-ethoxy-4-carboxylate
29. p-phenylene 2,2,6,6-tetramethylpiperidine-4-carboxylate
30. p-xylylene 2,2,6,6-tetramethylpiperidine-4-carboxylate
31. methyl 1-methyl-2,2,6,6-tetramethylpiperidine-4-carboxylate
32. n-butyl 1-ethyl-2,2,6,6-tetramethylpiperidine-4-hydroxy-4-carboxylate
33. ethyl-1-methyl-2,2,6,6-tetramethylpiperidine-4-methoxy-4-carboxylate
34. p-phenylene 1-methyl-2,2,6,6-tetramethylpiperidine-4-hydroxy-4-carboxylate
35. p-xylylene 1-butyl-2,2,6,6-tetramethylpiperidine-4-methoxy-4-carboxylate, and the like.

The compounds of the invention may be incorporated into the polymer substrate by any of the various standard procedures commonly used in the art, at any stage prior to the manufacture of shaped articles therefrom, including filaments, fibre, yarn, film, sheet, other molded articles, and the like. Thus, the mixing, extrusion, etc. or a suspension or emulsion of the stabilizer may be mixed with a suspension or emulsion of the polymer, and the like.

The amount of the esters of formula (I) which may be incorporated into the polymer may vary widely depending on the type, properties and particular uses of the polymer to be stabilized. In general, they may be added in amounts ranging from about 0.01 to 5% by weight based on the polymer, preferably about 0.01 to 2% by weight, and preferably 0.01 to 1% by weight in polyolefins.

The compounds may be used alone or in combination with other known stabilizers, fillers, or other compounding ingredients commonly used.

We claim:
1. A compound represented by the formula:

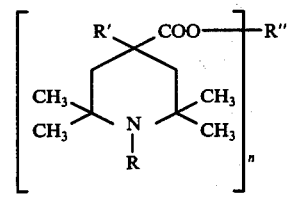

wherein R is hydrogen or alkyl ($C_1$–$C_8$), R' is hydrogen, or lower alkoxy ($C_1$–$C_8$); R" is alkylene ($C_2$–$C_{12}$), cycloalkylene, wherein the alicyclic ring may contain lower alkyl substituents, arylene or aralkylene, n is 2.

2. A compound as defined in claim 1 wherein R' is hydrogen.
3. A compound as defined in claim 1 wherein R' is lower ($C_1$–$C_8$) alkoxy.
4. A synthetic polyolefin polymer composition stabilized against photo- and thermal degradation comprising an effective stabilizing amount of a compound of claim 1.
5. A composition as defined in claim 4 wherein said polyolefin is polypropylene.
6. A composition as defined in claim 4 wherein said compound is incorporated in an amount of about 0.01 to 5% by weight.
7. A composition as defined in claim 5 wherein said compound is incorporated in an amount of about 0.01 to 2% by weight.
8. A compound as defined in claim 1 wherein R is hydrogen.
9. A compound as defined in claim 1 wherein R" is alkylene ($C_2$–$C_{12}$).

* * * * *